US00PP32086P3

(12) United States Plant Patent
Schoemaker

(10) Patent No.: US PP32,086 P3
(45) Date of Patent: Aug. 18, 2020

(54) ***HYDRANGEA* PLANT NAMED 'LC NO7'**

(50) Latin Name: *Hydrangea paniculata*
Varietal Denomination: LC NO7

(71) Applicant: Alex Frederick Schoemaker, Boskoop (NL)

(72) Inventor: Alex Frederick Schoemaker, Boskoop (NL)

( * ) Notice: Subject to any disclaimer, the term of this patent is extended or adjusted under 35 U.S.C. 154(b) by 0 days.

(21) Appl. No.: 16/602,283

(22) Filed: Sep. 6, 2019

(65) Prior Publication Data

US 2020/0084944 P1 Mar. 12, 2020

Related U.S. Application Data

(60) Provisional application No. 62/765,663, filed on Sep. 7, 2018.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 6/48
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'LC NO7', characterized by its medium size and broadly upright plant habit; freely branching habit with strong lateral branches; freely flowering habit with plants remaining in flower for a long period time; dense and hardy inflorescences with white-colored sterile flowers that age attractively to greyed purple in color with development; and good garden performance.

2 Drawing Sheets

Figure 1:
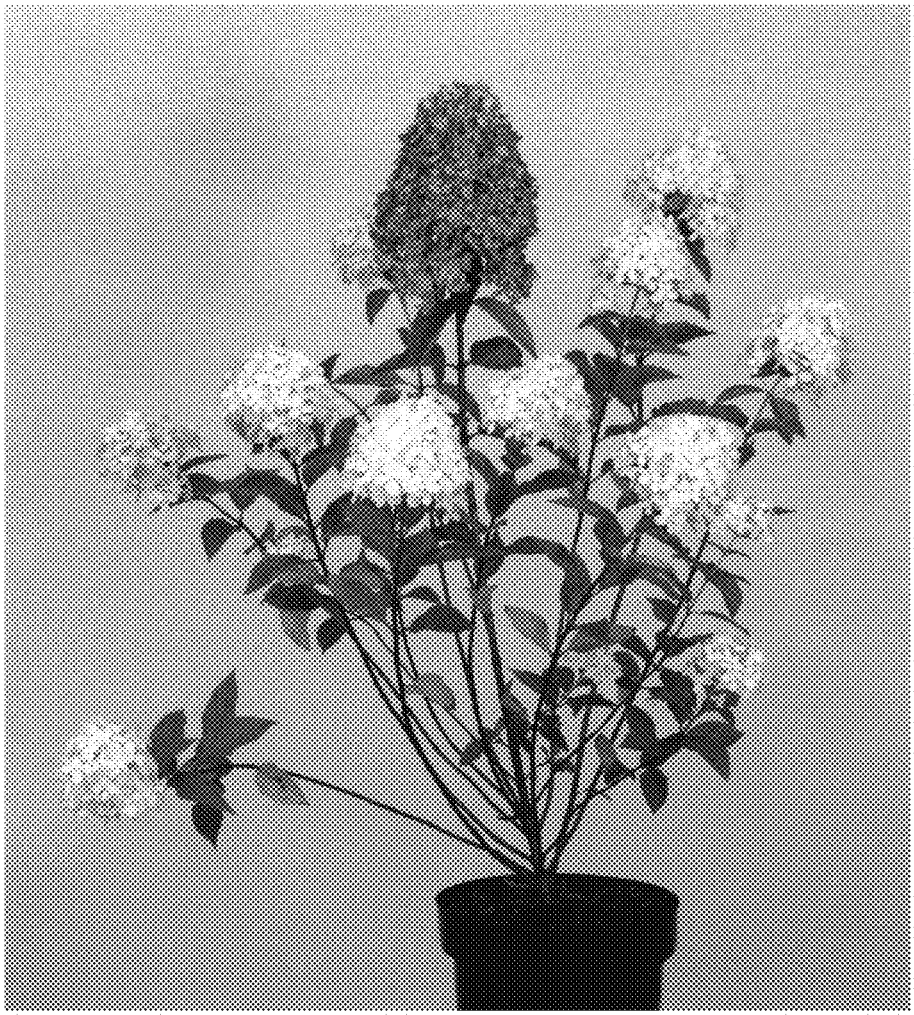

Botanical designation: *Hydrangea paniculata.*
Cultivar denomination: 'LC NO7'.

CROSS-REFERENCED TO CLOSELY RELATED APPLICATIONS

Title: Varieties of *Hydrangea* Plants
Applicant: Alex Frederick Schoemaker
Provisional application Ser. No. 62/765,663
Filed: Sep. 7, 2018
Title: *Hydrangea* Plant Named 'LC NO2'
Applicant: Alex Frederick Schoemaker
Filed: Plant patent application Ser. No. 16/602,287
Title: *Hydrangea* Plant Named 'LC NO5'
Applicant: Alex Frederick Schoemaker
Filed: Plant patent application Ser. No. 16/602,282

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO7'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from an open-pollination in July, 2013 in Boskoop, The Netherlands, of *Hydrangea paniculata* 'Limelight', disclosed in U.S. Plant Pat. No. 12,874, as the female, or seed, parent with an unknown selection of *Hydrangea paniculata* as the male, or pollen, parent. The new *Hydrangea* plant was discovered and selected by the Inventor as a single flowering plant from within the progeny of the stated open-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO7'. These characteristics in combination distinguish 'LC NO7' as a new and distinct *Hydrangea* plant:

1. Medium in size and broadly upright plant habit.
2. Freely branching habit with strong lateral branches.
3. Freely flowering habit with plants remaining in flower for a long period time.
4. Dense and hardy inflorescences with white-colored sterile flowers that age attractively to greyed purple in color with development.
5. Good garden performance.

Plants of the new *Hydrangea* can be compared to plants of the female parent, 'Limelight'. Plants of the new *Hydrangea* differ primarily from plants of 'Limelight' in the following characteristics:

1. Sterile flowers of plants of the new *Hydrangea* are smaller than sterile flowers of plants of 'Limelight'.
2. Plants of the new *Hydrangea* and 'Limelight' differ in sterile flower color as sterile flowers of plants of the new *Hydrangea* are white in color becoming greyed purple with development whereas sterile flowers of plants of 'Limelight' are light green in color.

Plants of the new *Hydrangea* can be compared to plants of the *Hydrangea paniculata* 'LC NO2', disclosed in a U.S. Plant Patent application filed concurrently. In side-by-side comparisons, plants of the new *Hydrangea* differ primarily from plants of 'LC NO2' in plant habit as plants of the new *Hydrangea* are taller and broader than plants of 'LC NO2'. In addition, plants of the new *Hydrangea* are more freely branching than plants of 'LC NO2'.

Plants of the new *Hydrangea* can be compared to plants of the *Hydrangea paniculata* 'LC NO5', disclosed in a U.S. Plant Patent application filed concurrently. In side-by-side comparisons, plants of the new *Hydrangea* differ primarily from plants of 'LC NO5' in plant habit as plants of the new *Hydrangea* are taller and broader than plants of 'LC NO5'. In addition, plants of the new *Hydrangea* are more freely branching than plants of 'LC NO5'.

Plants of the new *Hydrangea* can also be compared to plants of the *Hydrangea paniculata* 'Jane', disclosed in U.S. Plant Pat. No. 22,330. In side-by-side comparisons, plants of the new *Hydrangea* differ primarily from plants of 'Jane' in the following characteristics:

1. Leaf margins of plants of the new *Hydrangea* are more serrated than leaf margins of plants of 'Jane'.
2. Leaf apices of plants of the new *Hydrangea* are more pointed than leaf apices of plants of 'Jane'.
3. Leaves of plants of the new *Hydrangea* are matte in luster whereas leaves of plants of 'Jane' are glossy.
4. Sterile flowers of plants of the new *Hydrangea* are white in color becoming greyed purple in color with development whereas sterile flowers of plants of 'Jane' are light green in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'LC NO7'.

Figure 2:
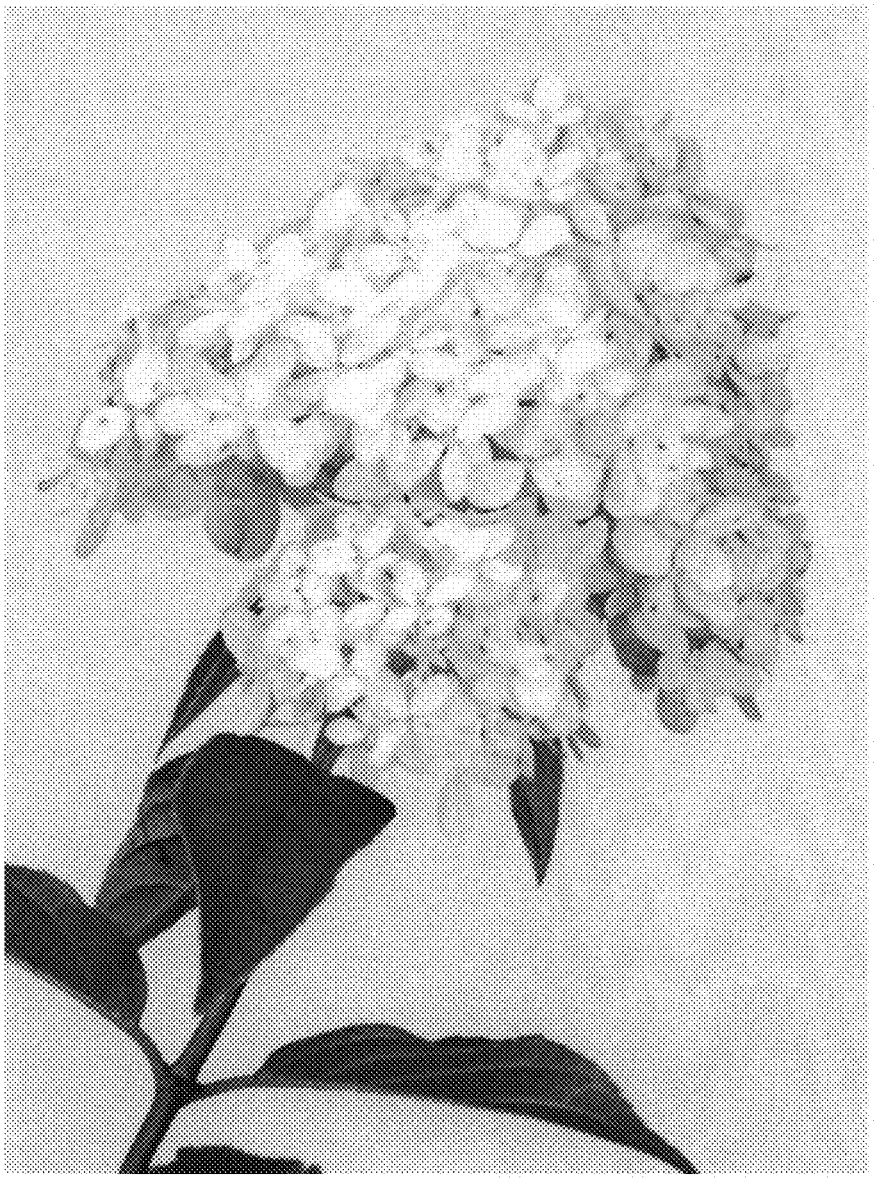

The photograph on the second sheet (FIG. 2 of 2) is a close-up view of a typical inflorescence of 'LC NO7'.

DETAILED BOTANICAL DESCRIPTION

Plants used in the aforementioned photographs and in the following description were grown during the late summer in 20-cm containers in an outdoor nursery in Boskoop, The Netherlands and under cultural practices typical of commercial *Hydrangea* production. During the production of the plants, day temperatures ranged from about 16° C. to 25° C. and night temperatures ranged from about averaged 5° C. to 16° C. Plants of the new *Hydrangea* were pinched one time and were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO7'.

Parentage:

*Female, or seed, parent.*—*Hydrangea paniculata* 'Limelight', disclosed in U.S. Plant Pat. No. 12,874.

*Male, or pollen, parent.*—Unknown selection of *Hydrangea paniculata*, not patented.

Propagation:

*Type cutting.*—By vegetative tip cuttings.

*Time to initiate roots, summer.*—About 20 days at temperatures about 16° C. to 30° C.

*Time to produce a rooted young plant, summer.*—About 50 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Medium-sized, broadly upright plant habit; overall plant shape, obovate to broadly obovate; strong and sturdy stems; moderately vigorous to vigorous growth habit and moderate to rapid growth rate.

*Plant height.*—About 74.8 cm.

*Plant diameter or area of spread.*—About 71 cm.

Lateral branch description:

*Branching habit.*—Freely branching habit, about 16 lateral branches develop per plant; pinching will enhance lateral branch development.

*Length.*—About 52.8 cm.

*Diameter.*—About 5 mm.

*Internode length.*—About 4.4 cm.

*Texture.*—When developing, densely pubescent; fully developed, woody.

*Aspect.*—Upright to about 40° from vertical.

*Strength.*—Strong, sturdy.

*Color.*—When developing: Close to a blend of N148D and 151D; surfaces exposed to sunlight are tinged with close to 182C to 182D. Developed: Close to a blend of N199B and 200C; when woody, close to N199B to N199C and 200D.

*Lenticels.*—Density: Sparse; only observed on developed stems. Size, developed stems: About 1.5 mm by 0.75 mm. Color, developed stems: Close to 173D.

Leaf description:

*Arrangement.*—Opposite, simple.

*Length.*—About 8 cm.

*Width.*—About 4 cm.

*Shape.*—Ovate.

*Apex.*—Apiculate.

*Base.*—Obtuse.

*Margin.*—Serrate.

*Texture, upper and lower surfaces.*—Moderately pubescent, scabrous; slightly rugose.

*Venation pattern.*—Pinnate.

*Color.*—Developing leaves, upper surface: Close to 144A. Developing leaves, lower surface: Close to between 145A and 147D. Fully developed leaves, upper surface: Close to between 143A and 144A; venation, close to 152B. Fully developed leaves, lower surface: Close to between 146D and 147C; venation, close to 195B to 195C proximally tinged with close to 182C.

*Petioles*.—Length: About 1 cm. Diameter: About 2 mm. Texture, upper and lower surfaces: Sparsely pubescent. Color, upper surface: Close to 182B; margins, close to 183B. Color, lower surface: Close to 153D tinged with close to 182C to 182D.

Flower description:

*Flower type and habit*.—Showy sterile flowers and small inconspicuous fertile flowers arranged on terminal panicles; panicles broadly ovate in shape; sterile flowers face upright to outwardly and slightly drooping depending on their position in the inflorescence; fertile flowers face mostly upright.

*Fragrance*.—Faintly fragrant; sweet and pleasant.

*Natural flowering season*.—Flowering begins in the midsummer and is continuous until late summer in Northern Europe.

*Flower longevity*.—Sterile flowers last about six weeks on the plant, sterile flowers persistent; fertile flowers last about five days on the plant, fertile flowers not persistent.

*Quantity of flowers*.—Freely flowering habit; about 400 sterile flowers and about 140 fertile flowers per panicle.

*Panicle height*.—About 13.9 cm.

*Panicle diameter*.—About 12.8 cm.

*Sterile flower buds*.—Length: About 5 mm. Diameter: About 1 cm. Shape: Cup-shaped. Color: Close to 157C.

*Fertile flower buds*.—Length: About 4 mm. Diameter: About 2 mm. Shape: Obovate. Color: Close to NN155D; towards the apex, close to N66C; immature calyx, close to 155A.

*Sterile flower diameter*.—About 2.5 cm.

*Sterile flower depth* (*height*).—About 5 mm.

*Fertile flower diameter*.—About 8 mm.

*Fertile flower depth* (*height*).—About 5 mm.

*Petals, sterile flowers*.—Quantity and arrangement: Four in a single whorl. Length: About 2.5 mm. Width: About 1.5 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155D; towards the apex, tinged with close to 68B; color does not change with development.

*Petals, fertile flowers*.—Quantity and arrangement: Five in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155D; towards the apex, slightly tinged with close to 68B; color does not change with development.

*Sepals, sterile flowers*.—Quantity and arrangement: Typically four, occasionally three, in a single whorl. Length: About 1.35 cm. Width: About 8 mm. Shape: Obovate to elliptic. Apex: Rounded to emarginate. Base: Cuneate. Margin: Entire. Texture and luster, upper and lower surfaces: Smooth, glabrous; matte. Color: When opening, upper and lower surfaces: Close to NN155B. Fully opened, upper and lower surfaces: Close to NN155B; color becoming closer to 185C with development.

*Sepals, fertile flowers*.—Quantity and arrangement: Five in a single whorl. Length: About 1 mm. Width: About 1 mm. Shape: Near deltoid. Apex: Broadly acuminate. Base: Broadly cuneate. Margin: Entire. Texture and luster, upper and lower surfaces: Smooth, glabrous; matte. Color: When opening and fully opened, upper surface: Close to 155C; color does not change with development. When opening and fully opened, lower surface: Close to 155C; color does not change with development.

*Pedicels, sterile flowers*.—Length: About 1.5 cm. Diameter: About 1 mm. Strength: Moderately strong. Aspect: About 60° from branch axis. Texture and luster: Sparsely pubescent; matte. Color: Close to NN155B.

*Pedicels, fertile flowers*.—Length: About 1 mm. Diameter: About 0.5 mm. Strength: Moderately strong. Aspect: About 10° from branch axis. Texture and luster: Densely pubescent; matte. Color: Close to 155C.

*Reproductive organs, sterile flowers*.—Stamens: Quantity per flower: About ten. Filament length: About 2.5 mm. Filament color: Close to NN155D. Anther length: About 0.5 mm. Anther shape: Broadly oblong. Anther color: Close to 155A. Pollen amount: Moderate. Pollen color: Close to 155A. Pistils: To date, pistil development on sterile flowers of the new *Hydrangea* has not been observed.

*Reproductive organs, fertile flowers*.—Stamens: Quantity per flower: About ten. Filament length: About 4 mm. Filament color: Close to NN155D. Anther length: About 0.5 mm. Anther shape: Broadly oblong. Anther color: Close to 155A. Pollen amount: Moderate. Pollen color: Close to 156A. Pistils: Pistil quantity per flower: Typically three, occasionally two. Pistil length: About 1 mm. Stigma shape: Club-shaped. Stigma color: Close to 155C. Style length: About 0.5 mm. Style color: Close to 155C. Ovary color: Close to 157A.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO7' as illustrated and described.

* * * * *